(12) United States Patent
Brand et al.

(10) Patent No.: US 10,092,717 B2
(45) Date of Patent: Oct. 9, 2018

(54) METHOD AND APPARATUS FOR INCREASING COUGH FLOW

(71) Applicant: KONINKLIJKE PHILIPS N.V., Eindhoven (NL)

(72) Inventors: Maarten Leonardus Christian Brand, Murrysville, PA (US); Wei Zhou, Shanghai (CN); Huimin Chen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 827 days.

(21) Appl. No.: 14/376,148

(22) PCT Filed: Feb. 6, 2013

(86) PCT No.: PCT/IB2013/050982
§ 371 (c)(1),
(2) Date: Aug. 1, 2014

(87) PCT Pub. No.: WO2013/118061
PCT Pub. Date: Aug. 15, 2013

(65) Prior Publication Data
US 2014/0373844 A1    Dec. 25, 2014

(30) Foreign Application Priority Data

Feb. 8, 2012    (CN) .......................... CN2012/070954

(51) Int. Cl.
*A61M 16/00*    (2006.01)
*A61M 16/06*    (2006.01)
(Continued)

(52) U.S. Cl.
CPC .... *A61M 16/0069* (2014.02); *A61M 16/0003* (2014.02); *A61M 16/0006* (2014.02);
(Continued)

(58) Field of Classification Search
CPC .......... A61M 16/0006; A61M 16/0069; A61B 5/0823
See application file for complete search history.

(56) References Cited

U.S. PATENT DOCUMENTS 5,280,784 A    1/1994    Kohler
5,345,930 A    9/1994    Cardinal
(Continued)

FOREIGN PATENT DOCUMENTS

CN    2698353 Y    5/2005
CN    1010222847 A    8/2007
(Continued)

OTHER PUBLICATIONS

Hogg J. C. (2004). "Pathophysiology of Airflow Limitation in Chronic Obstructive Pulmonary Disease." The Lancet, vol. 364, Aug. 21, 2004, pp. 709-721.
(Continued)

*Primary Examiner* — Jackie Tan-Uyen T Ho
*Assistant Examiner* — Joseph D Boecker
(74) *Attorney, Agent, or Firm* — Michael W. Haas

(57) ABSTRACT

A system and method are configured to utilize patient effort to increase cough flow of a subject by limiting airway collapse by causing a series of exsufflation events over an individual exhalation of the subject. A single exhalation of the subject is segmented into a series of exsufflation events by a processor configured to toggle a pressure regulator between a first airway closed mode and a second airway open mode. The processor is configured such that the transitions between the closed and open modes are initiated based on predetermined timing or based on output signals generated by sensors monitoring one or more gas parameters (for example, pressure) in the airway of the patient.

15 Claims, 3 Drawing Sheets

(51) Int. Cl.
*A61M 16/08* (2006.01)
*A61M 16/16* (2006.01)
*A61B 5/08* (2006.01)

(52) U.S. Cl.
CPC .... *A61M 16/0009* (2014.02); *A61M 16/0051* (2013.01); *A61M 16/024* (2017.08); *A61M 16/06* (2013.01); *A61M 16/0875* (2013.01); *A61M 16/161* (2014.02); *A61B 5/0823* (2013.01); *A61M 2016/0027* (2013.01); *A61M 2016/0033* (2013.01); *A61M 2205/3344* (2013.01); *A61M 2205/3368* (2013.01); *A61M 2205/502* (2013.01); *A61M 2230/43* (2013.01)

(56) References Cited

U.S. PATENT DOCUMENTS

| | | | |
|---|---|---|---|
| 6,176,235 B1 * | 1/2001 | Benarrouch | A61F 11/00 128/200.24 |
| 6,210,345 B1 * | 4/2001 | Van Brunt | A61H 9/0078 600/529 |
| 2005/0051174 A1 * | 3/2005 | Emerson | A61M 16/0057 128/207.14 |
| 2005/0126578 A1 | 6/2005 | Garrison | |
| 2008/0023005 A1 | 1/2008 | Tokunaga | |
| 2010/0122699 A1 * | 5/2010 | Birnkrant | A61M 1/0023 128/204.21 |
| 2010/0180897 A1 * | 7/2010 | Malgouyres | A61M 16/00 128/204.23 |
| 2011/0220107 A1 * | 9/2011 | Kimm | A61M 16/00 128/204.21 |

FOREIGN PATENT DOCUMENTS

| | | |
|---|---|---|
| JP | 2003079732 A | 3/2003 |
| WO | WO2011010279 A1 | 1/2011 |

OTHER PUBLICATIONS

Malik S.K. et al., "Alterations in Airway Dynamics Following Inhalation of Ultrasonic Mist." Clinical Investigation, Chest, vol. 62, No. 6, Dec. 1972, pp. 660-664 http://journal.publications.chestnet.org.

Khan S.Y. et al., "Is Nebulized Saline a Placebo in COPD?", BMC Pulmonary Medicine 2004, BioMed Central, vol. 4, No. 9, Sep. 30, 2004 http://www.biomedcentral.com/1471-2466/4/9/prepub.

Yanai M. et al., "Deposition and Clearance of Inhaled 18FDG Powder in Patients with Chronic Obstructive Pulmonary Disease", European Respiratory Journals Ltd 1998, vol. 11, pp. 1342-1348.

Sala H. et al., "Supramaximal Flow in Asthmatic Patients", European Respiratory Journals Ltd 2002, vol. 19, pp. 1003-1007.

Pedersen O.F. et al., "Airway Dynamics in Transition Between Peak and Maximal Expiratory Flow", Institutes of Hygiene and Physiology, University of Aarhus, DK-8000 Aarhus C, Denmark; The American Physiological Society, Apr. 1985, pp. 1733-1746.

* cited by examiner

METHOD AND APPARATUS FOR INCREASING COUGH FLOW

CROSS-REFERENCE TO RELATED APPLICATIONS

This patent application claims the priority benefit under 35 U.S.C. § 371 of international patent application no. PCT/IB2013/050982, filed Feb. 6, 2013, which claims the priority benefit of CN Application No. PCT/CN2012/070954 filed on Feb. 8, 2012, the contents of which are herein incorporated by reference.

BACKGROUND

1. Field

The present disclosure pertains to a method and apparatus for increasing cough flow of a subject by transforming a single cough of the subject into multiple coughs of smaller duration during an individual exhalation.

2. Description of the Related Art

Various systems for increasing patient cough flow through exsufflation are known. Conventional exsufflation is generally accomplished using a single exsufflation event over a single exhalation of the subject. A respiratory circuit may be pressurized by the subject, and then the circuit may be opened once, while all (or substantially all) of the gas that pressurized the circuit is expelled there through. Secretions built up in the airway of the subject over time may be expelled with the gas.

SUMMARY

Accordingly, one or more aspects of the present disclosure relate to a device configured to enhance cough flow of a subject. In some embodiments, the device comprises a subject interface, a pressure regulator, and a controller configured to operate the pressure regulator. The subject interface is configured to communicate with an airway of the subject. The pressure regulator is configured to selectively control flow through the subject interface. The pressure regulator is configured to operate in (i) a first mode in which the subject interface is closed such that substantially no gas is communicated with the airway of the subject therethrough, and (ii) a second mode in which the subject interface is opened to permit gas to be exhausted from the airway of the subject through the subject interface. The controller configured to operate the pressure regulator is configured such that during an individual exhalation of the subject, the pressure regulator is toggled between the first mode and the second mode to cause a series of exsufflation events for the individual exhalation of the subject.

Yet another aspect of the present disclosure relates to a method of enhancing the cough flow of a subject. In some embodiments, the method comprises interfacing with an airway of the subject with a subject interface; operating a pressure regulator in a first mode in which the subject interface is closed such that substantially no gas is communicated with the airway of the subject therethrough; receiving information indicating pressurization of the subject interface by the subject; and exsufflating the subject with a series of exsufflation events by toggling the pressure regulator between the first mode and a second mode to create a series of exsufflation events during a single exhalation, wherein in the second mode the subject interface is opened to permit gas to be exhausted from the airway of the subject through the subject interface.

Still another aspect of present disclosure relates to a system configured to enhance the cough flow of a subject. In some embodiments, the system comprises means for communicating with an airway of the subject; means for selectively controlling flow through the means for communicating, the means for selectively regulating flow operating in (i) a first mode in which the means for communicating is closed such that substantially no gas is communicated with the airway of the subject therethrough, and (ii) a second mode in which the means for communicating is opened to permit gas to be exhausted from the airway of the subject through the means for communicating; means for receiving information indicating whether the subject has pressurized the means for communicating; means for determining whether the means for communicating is pressurized based on the received information; and means for controlling operation of the means for selectively controlling flow between the first mode and the second mode to exsufflate the subject, wherein the means for controlling the means for selectively regulating exsufflate the subject by placing the means for selectively regulating in the first mode until a determination by the means for determining determines that the subject has pressurized the means for communicating, and, responsive to such a determination, causes a series of exsufflation events over an individual exhalation of the subject by toggling the means for regulating between the first mode and the second mode during the individual exhalation.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
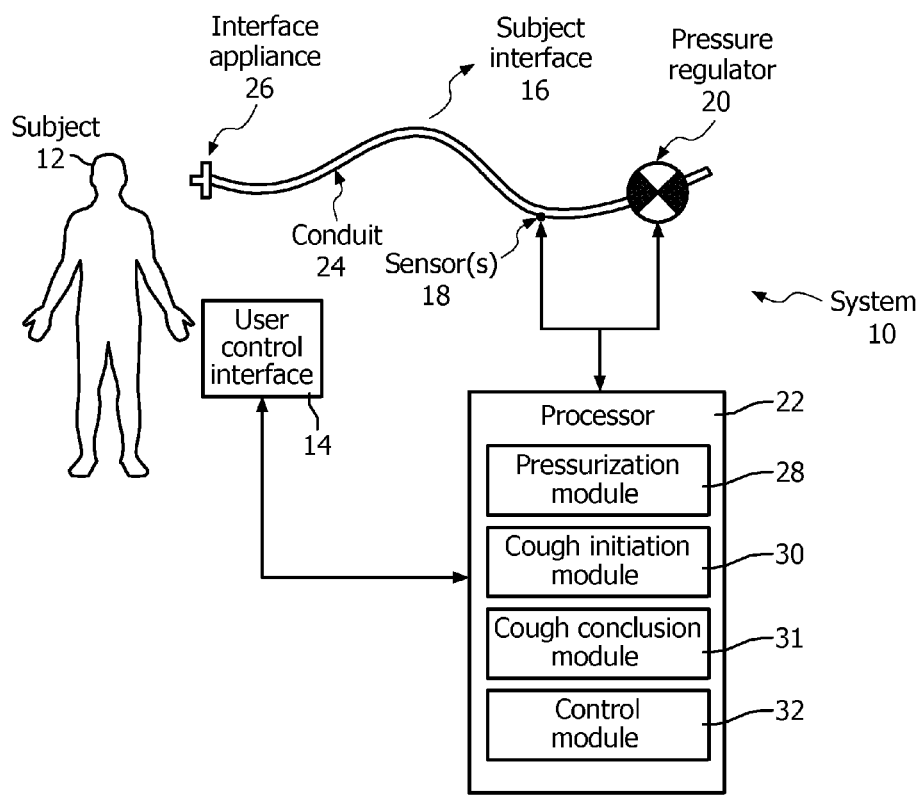
FIG. 1 is a system configured to increase cough flow of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 to enhance cough flow of a subject 12. System 10 enhances flow during exsufflation by, among other things, limiting airway collapse of subject 12. System 10 utilizes patient effort to pressurize system 10, and causes a series of exsufflation events over an individual exhalation of subject 12. The exsufflation events are short pulses during which air is allowed to flow out of the lungs of the subject. Segmentation of exsufflation into a series of exsufflation events may tend to increase flow over the exhalation, and/or may loosen and/or expel secretions with an enhanced effectiveness. In some embodiments, system 10 includes one or more of a subject 12, a user control interface 14, a subject interface 16, one or more sensors 18, a pressure regulator 20, a processor 22, and/or other components.

User control interface 14 is configured to provide an interface between system 10 and subject 12 through which subject 12 provides information to and receives information from system 10. This enables data, results, and/or instructions and any other communicable items, collectively referred to as "information," to be communicated between the subject 12 and one or more of subject interface 16, and/or processor 22. Examples of interface devices suitable for inclusion in user control interface 14 include a keypad, buttons, switches, a keyboard, knobs, levers, a display screen, a touch screen, speakers, a microphone, an indicator light, an audible alarm, a printer, a tactile feedback device, a gesture recognition device, and/or other interface devices. For example, in some implementations subject 12 pushes a button to communicate to processor 22 that pressure is built in subject interface 16. In one embodiment, user control interface 14 includes a plurality of separate interfaces. For example, system 10 may be configured with the push button mentioned above, and/or a gesture (e.g.; facial movement such as blinking) recognition device for use by a subject who may not have full physical control of their extremities (e.g., a fully or partially paralyzed subject).

It is to be understood that other communication techniques, either hard-wired or wireless, are also contemplated by the present invention as user control interface 14. For example, the present invention contemplates that user control interface 14 is a remote control. In this example, information indicating a pressurized subject user interface is wirelessly transmitted to processor 22 that enables the user to begin the segmented exsufflation process controlled by system 10. Other exemplary input devices and techniques adapted for use with system 10 as user control interface 14 include, but are not limited to, an RS-232 port, RF link, an IR link, modem (telephone, cable or other). In short, any technique for communicating information with system 10 is contemplated by the present invention as user control interface 14.

Subject interface 16 is configured to interface with the airway of subject 12. Subject interface 16 is configured to provide fluid communication with the airway of subject 12. As such, subject interface 16 includes a conduit 24 and/or an interface appliance 26. Conduit 24 conveys gas (e.g., air) to and/or from interface appliance 26, and interface appliance 26 places conduit 24 in communication with the airway of subject 12. In some embodiments, subject interface 16 is non-invasive. As such, interface appliance 26 non-invasively engages subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Some examples of non-invasive interface appliance 26 may include, for example, a blow tube, a nasal cannula, a nasal mask, a nasal/oral mask, a full face mask, a total face mask, or other interface appliances that communicate a flow of gas with an airway of a subject.

Sensors 18 are configured to generate output signals conveying information related to one or more gas parameters of the gas within subject interface 16. The one or more gas parameters comprise flow, volume, pressure, temperature, humidity, velocity, and/or other gas parameters. Gas parameter sensors 18 may comprise one or more sensors that measure such parameters directly (e.g., through fluid communication with the flow of gas in subject interface 16). Gas parameter sensors 18 may comprise one or more sensors that generate output signals related to one or more parameters of the flow of gas indirectly. For example, one or more of sensors 18 may generate an output based on an operating parameter of the pressure regulator 20 (e.g., a valve driver or motor current, voltage, rotational velocity, and/or other operating parameters), and/or other sensors. Although gas parameter sensors 18 are illustrated at a single location within (or in communication with) conduit 24 between interface appliance 26 and pressure regulator 20, this is not intended to be limiting. Gas parameter sensors 18 may include sensors disposed in a plurality of locations, such as for example, within pressure regulator 20, within (or in communication with) interface appliance 26, and/or other locations.

Pressure regulator 20 is configured to selectively control flow through subject interface 16. Pressure regulator 20 is configured to operate in a first mode, a second mode, and/or in other modes. In the first mode, subject interface 16 is closed such that substantially no gas is communicated with the airway of the subject therethrough. In the second mode the subject interface is opened to permit gas to be exhausted from the airway of the subject through subject interface 16.

In some implementations pressure regulator 20 may comprise one or more of a valve and/or another pressure regulating device. In one embodiment pressure regulator 20 may comprise one or more valves in series and/or in parallel. Examples of valves and/or other pressure regulating devices suitable for inclusion in pressure regulator 20 include, a plug valve, a ball valve, a check valve, a butterfly valve, a solenoid, and/or other pressure regulating devices The pressure regulating devices mentioned above and/or other pressure regulating devices that may be included in pressure regulator 20 may be controlled hydraulically, pneumatically, via an electric motor and/or another mode of control configured to open and/or close a valve and/or other pressure control device.

In some implementations pressure regulator 20 may be located at one or more locations in system 10. For example, in one embodiment pressure regulator 20 may be located at one end of subject interface 16, opposite interface appliance 26. In a second embodiment pressure regulator 20 may be located between interface appliance 26 and conduit 24.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 includes a plurality of processing units. These processing units may be physically located within the same device, or processor 22 may represent processing functionality of a plurality of devices operating in coordination. In some implementations, communication between processors and/or sensor(s) 18 occurs wirelessly or via wires.

As is shown in FIG. 1, processor 22 may be configured to execute one or more computer program modules. The one or more computer program modules comprise one or more of a pressurization module 28, a cough initiation module 30, a cough conclusion module 31, a control module 32, and/or other modules. Processor 22 may be configured to execute modules 28, 30, 31 and/or 32 by software; hardware; firmware; some combination of software, hardware, and/or firmware; and/or other mechanisms for configuring processing capabilities on processor 22.

It should be appreciated that although modules 28, 30, 31 and 32 are illustrated in FIG. 1 as being co-located within a single processing unit, in implementations in which processor 22 includes multiple processing units, one or more of modules 28, 30, 31 and/or 32 may be located remotely from the other modules. The description of the functionality provided by the different modules 28, 30, 31 and/or 32 described below is for illustrative purposes, and is not intended to be limiting, as any of modules 28, 30, 31 and/or 32 may provide more or less functionality than is described. For example, one or more of modules 28, 30, 31 and/or 32 may be eliminated, and some or all of its functionality may be provided by other ones of modules 28, 30, 31 and/or 32. As another example, processor 22 may be configured to execute one or more additional modules that may perform some or all of the functionality attributed below to one of modules 28, 30, 31 and/or 32.

Pressurization module 28 is configured to receive information indicating whether respiratory effort of subject 12 (e.g., unassisted respiratory effort) has pressurized subject interface 16. Based on the received information, pressurization module 28 determines whether subject interface 16 is pressurized. In some embodiments, pressurization module 28 is configured such that the information indicating whether subject 12 has pressurized subject interface 16 comprises an input by subject 12 to user control interface 14. For example, subject 12 pressurizes subject interface 16 by blowing on interface appliance 26 with pressure regulator 20 in the first mode (closed). After pressurization, subject 12 pushes a button of user control interface 14 (or otherwise engages some element of user control interface 14) to indicate that pressure is built in subject interface 16.

In some embodiments, pressurization module 28 is configured such that the information indicating whether the user has pressurized subject interface 16 comprises the output signals of sensors 18. For example, subject 12 pressurizes subject interface 16 by blowing on interface appliance 26 with pressure regulator 20 in the first mode (closed). In such embodiments, pressurization module 28 determines whether subject interface 16 is appropriately pressurized based on the one or more gas parameters for which information is conveyed by the output signals. For example, responsive to a level of a gas parameter breaching a threshold level, pressurization module 28 determines that subject interface 16 is pressurized.

Cough initiation module 30 is configured to detect a cough trigger event during normal breathing of subject 12 through subject interface 16. This breathing occurs while pressure regulator 20 is operating in the second mode so that subject 12 can inhale and exhale freely through subject interface 16. In some embodiments the information indicating a cough trigger event comprises one or more gas parameters (e.g. pressure, flow, and/or other gas parameters) concerning which information is conveyed by the output signals of sensors 18.

A cough trigger event may comprise output signals that indicate an inhalation in preparation for a cough by subject 12. Such an inhalation may be referred to as a preparatory inhalation. A preparatory inhalation may be distinguished from other inhalations of subject 12 through subject interface 16 in that a preparatory inhalation may be sharper (e.g., with a higher magnitude flow rate or a lower pressure) and/or deeper (e.g., with a higher volume of flow) that other inhalations by subject 12. In some embodiments, cough initiation module 30 is configured to detect a cough trigger event based on one or more gas parameters breaching a threshold level (e.g., pressure and/or flow breaching threshold(s)). The threshold levels may be configurable to a user (e.g., subject 12, a doctor, a caregiver, a researcher, and/or other users), predefined at manufacture, determined dynamically based on previous respiration by subject 12, and/or determined in other manners.

Cough conclusion module 31 is configured to detect cough conclusion after exsufflation of subject 12 through subject interface 16. Detection of a cough conclusion is made based on input received from subject 12 (e.g., input via user control interface 14 indicating the user is done with the cough), based on the output signals of sensor 18, and/or based on other parameters. Detecting a cough conclusion based on the output signals of sensor 18 may be made by monitoring the output signals for an indication of changes to one or more gas parameters within subject interface 16 indicating that the cough is concluding or has concluded (e.g., that the air in the lungs of subject 12 has been depleted). This may include monitoring one or more of pressure, flow rate, volume and/or other parameters over individual exsufflation events and/or groups of exsufflation events (e.g., for the entire cough, over a sliding window of n most recent events, etc.).

By way of non-limiting example, a cough conclusion may be detected based on a total exhaled volume over the span of the cough. Responsive to the total exhaled volume reaching a threshold amount, the cough conclusion may be detected. The threshold amount may be determined based on an inhaled volume in the inhalation prior to the cough, a user configurable setting, previous coughs by subject 12, and/or determined in other ways.

As another non-limiting example, one or more of pressure, flow rate, and/or volume of individual exsufflation events are monitored to detect a cough conclusion. Responsive to one or more of these parameters breaching a threshold level during an exsufflation event, the cough conclusion may be detected (e.g., not reaching a minimum pressure level, not reaching a minimum flow rate magnitude, not reaching a minimum volume, etc.). In some embodiments, a sliding window of n exsufflation events may be monitored, rather than an individual exsufflation event. In such embodiments, an aggregation (e.g., a sum, an average, a weighted average, etc.) of measurements taken during the individual exsufflation events within the sliding window are compared with a corresponding threshold level. The thresholds may be determined based on a user-configurable setting, based on previous respiration by subject 12 through subject interface 16, predetermined at manufacture, and/or determined in other ways.

As yet another non-limiting example, detection of a cough conclusion is made based on the passage of time. At some time amount after a cough trigger event, and/or a first exsufflation event the cough conclusion may be detected. The time amount may be determined based on a user-configurable setting, based on previous respiration by subject 12 through subject interface 16, predetermined at manufacture, and/or determined in other ways.

Control module 32 is configured to control operation of pressure regulator 20 between the first mode (closed) and the second mode (open) to exsufflate subject 12. Exsufflation is a forced release of gas from the lungs of subject 12. Control module 32 is configured to exsufflate subject 12 by placing pressure regulator 20 in the second (open) mode until a determination by cough initiation module 30 that subject 12 has experienced a cough trigger event. Responsive to such a determination, control module 32 is configured to place pressure regulator 20 in the first mode. As pressure regulator 20 is being operated in the first mode, respiratory effort by subject 12 into subject interface 16 will pressurize subject interface 16. This pressurization is monitored by pressurization module 28 as described above. Responsive to a determination by pressurization module 28 that subject 12 has pressurized subject interface 16 sufficient for a cough, control module 32 is configured to cause a series of segmented exsufflation events over an individual exhalation of subject 12. This exsufflation occurs through subject interface 16. The exsufflation events are created by toggling pressure regulator 20 between the first mode and the second mode during the individual exhalation. Responsive to a determination by cough conclusion module 31 that the cough has concluded, control module 32 is configured to place pressure regulator 20 in the second (open) mode and subject 12 may return to normal breathing.

Figure 2:
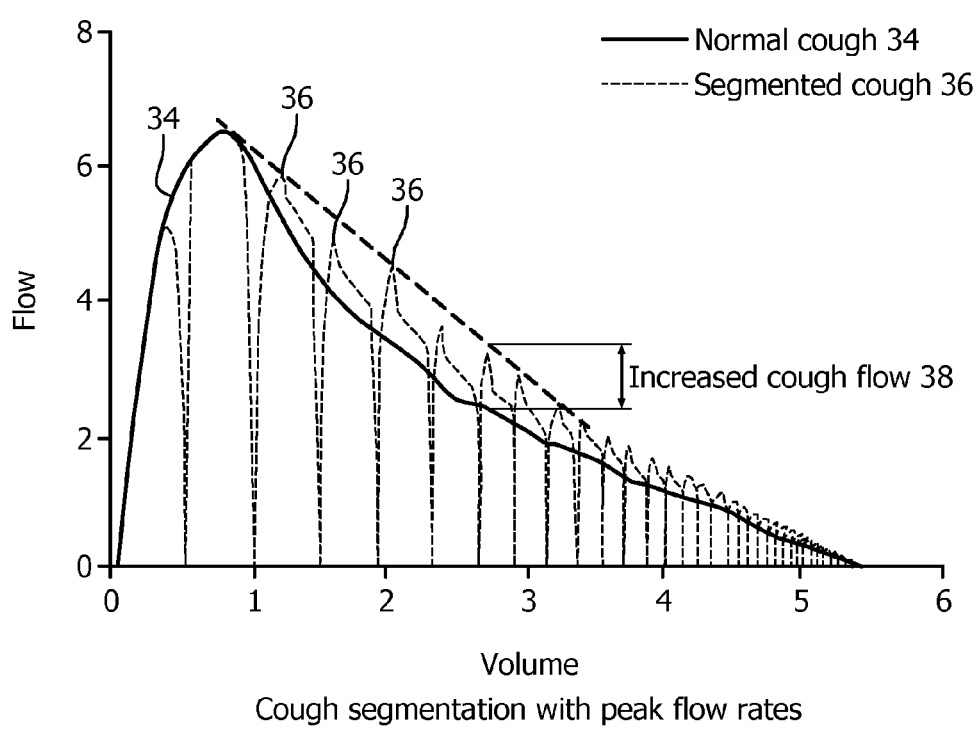
FIG. 2 is a graphical illustration of increased flow induced by a segmented cough.

By way of illustration, FIG. 2 shows a conventional exsufflation 34 compared to a segmented exsufflation 36 (e.g., including a series of exsufflation events). Flow during segmented exsufflation 36 rises above conventional exsufflation 34 at most of the individual exsufflation events. This may result in overall flow out of the lungs of a subject being greater, more forceful, and/or more effective at loosening and/or expelling secretions than the flow associated with conventional exsufflation 34.

Returning to FIG. 1, control module 32 controls one or more parameters of the exsufflation events in a segmented exsufflation. The one or more exsufflation parameters may include, for an individual exsufflation event, one or more of time in the first mode, time in the second mode, a transition from the first mode to the second mode (e.g., the timing of the transition), a transition from the second mode to the first mode (e.g., the timing of the transition), and/or other parameters.

In one embodiment, control module 32 is configured such that the transitions from first mode to second mode and/or the transitions from second mode to first mode are initiated based on predetermined timings. The predetermined timings may be based on a period frequency or period length, a standard length for the first mode, a standard length for the second mode, and/or other periodic timings. The predetermined timings may vary over the exhalation (e.g., longer exsufflation events at the beginning of the exhalation and shorter exsufflation events at the end of the exhalation). These timings may be configurable to a user (e.g., subject 12, a caregiver, a researcher, and/or other users). For example one or more user settings may be configurable to users via user control interface 14 to set such timings.

In one embodiment, control module 32 is configured such that the transitions from first mode to second mode and/or transitions from second mode to first mode are initiated based on the output signals generated by sensor 18. For example, subsequent to an initial exsufflation event, control module 32 may be configured to place pressure regulator 20 in the first mode of operation, thereby closing subject interface 16. Pressure regulator 20 may remain in the first mode of operation until respiratory effort by subject 12 against the closure of subject interface 14 causes one or more gas parameters to breach a threshold level (e.g., pressure to rise above a pressure threshold). Responsive to this, control module 32 may initiate a next exsufflation event by switching pressure regulator 20 from the first mode to the second mode of operation. As another example, while pressure regulator 20 is being operated in the second mode, control module 30 may switch such operation to the first mode responsive to the output signals of sensor 18 indicating that one or more gas parameters have breached a threshold level (e.g., pressure and/or flow falling below threshold(s)). The threshold levels may be may be configurable to a user (e.g., subject 12, a caregiver, a researcher, and/or other users). For example one or more user settings may be configurable to users via user control interface 14 to set such thresholds.

It will be appreciated that the description of the operation of pressure regulator 20 by the electronic processor 22 and/or its modules 28, 30, 32 is not intended to be limiting. Other controllers for opening pressure regulator 20 responsive to pressurization of subject interface 16, and/or toggling pressure regulator 20 between the first mode and the second mode to cause a plurality of exsufflation events over an individual exhalation fall within the scope of this disclosure. For example, one or more resilient members (e.g., a spring, a band, and/or other resilient members) (not shown) may operate to cause oscillation of pressure regulator 20 between the first mode and the second mode during the individual exhalation (e.g., the period of time during which gas is exhausted from the lungs of subject 12 without intervening inhalation). Other mechanical controllers are also contemplated.

Figure 3:
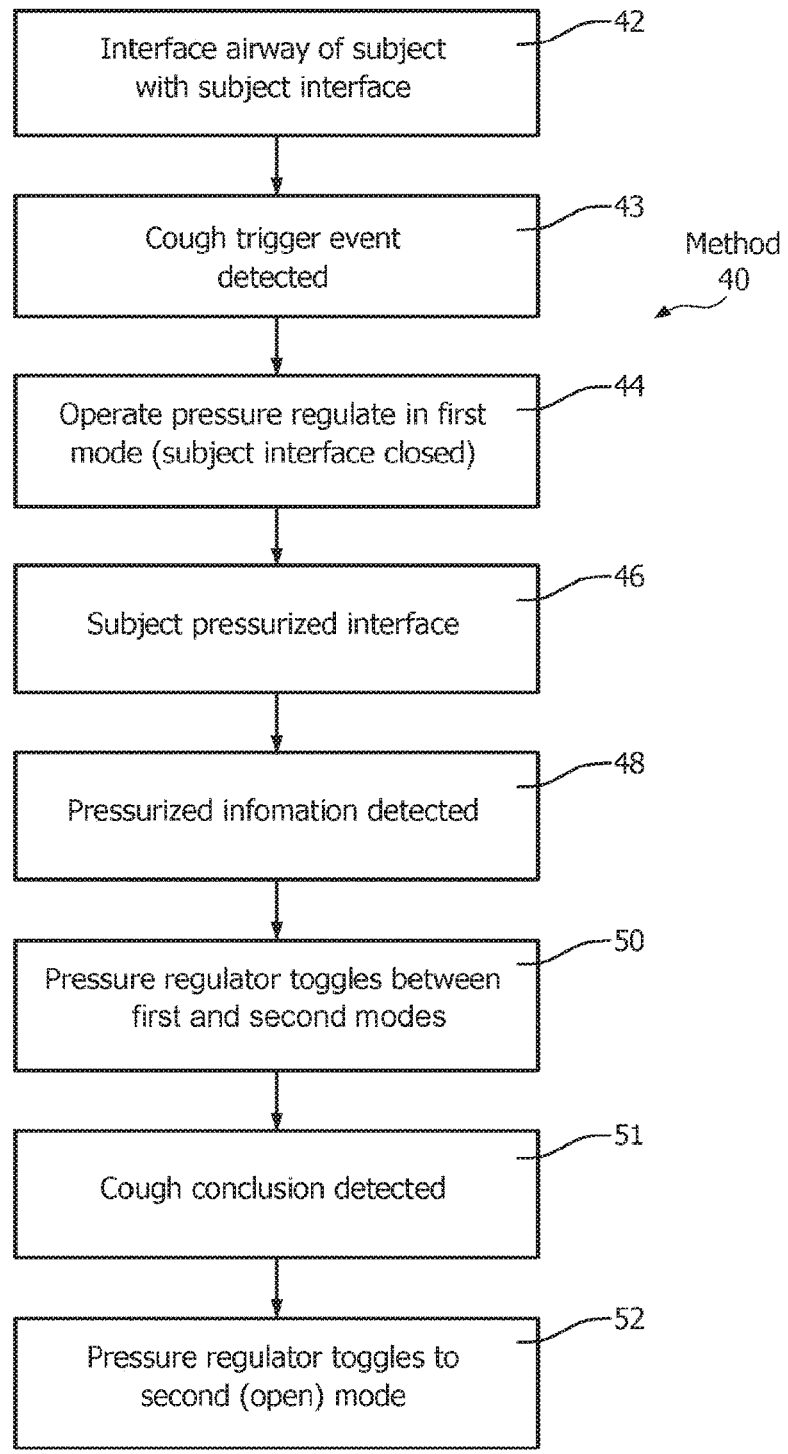
FIG. 3 is a method of increasing cough flow of a subject.

FIG. 3 illustrates a method 40 of monitoring and controlling a pressure support device to enhance cough flow of a subject. The operations of method 40 presented below are intended to be illustrative. In some embodiments, method 40 may be accomplished with one or more additional operations not described, and/or without one or more of the operations discussed. Additionally, the order in which the operations of method 40 are illustrated in FIG. 3 and described below is not intended to be limiting.

In some embodiments, method 40 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 40 in response to instructions stored electronically on an electronic storage medium. The one or more processing devices may include one or more devices configured through hardware, firmware, and/or software to be specifically designed for execution of one or more of the operations of method 40.

At an operation 42, a subject interface interfaces with the airway of a subject. In some embodiments, operation 42 is performed by a subject interface and/or interface appliance the same as or similar to subject interface 16 and/or interface appliance 26 (shown in FIG. 1 and described herein).

At an operation 43, information indicating a cough trigger event is detected. In some embodiments, operation 43 is performed by a processor the same as or similar to processor 22, (shown in FIG. 1 and described herein.)

At an operation 44, a pressure regulator operates in a first mode. In the first mode the subject interface is closed. In some embodiments, operation 44 is performed by a pressure regulator the same as or similar to pressure regulator 20 (shown in FIG. 1 and described herein).

At an operation 46, the subject interface is pressurized by a subject. The subject pressurizes the subject interface by exerting air pressure on the subject interface. In some embodiments, operation 46 is performed by a subject interface the same as or similar to subject interface 16 (shown in FIG. 1 and described herein.)

At an operation 48, information indicating pressurization of the subject interface by the subject is detected. In some embodiments, operation 48 is performed by a processor the same as or similar to processor 22, (shown in FIG. 1 and described herein).

At an operation 50, the pressure regulator toggles between the first closed mode and a second open mode. In the second mode the subject interface is opened to permit gas to be exhausted from the airway of the subject. Toggling between the first and second modes exsufflates the subject with a series of segmented exsufflation events during a single exhalation. In some embodiments, operation 50 is performed by a pressure regulator the same as or similar to pressure regulator 20, (shown in FIG. 1 and described herein).

At an operation 51, information indicating cough conclusion is detected. In some embodiments, operation 51 is performed by a processor the same as or similar to processor 22, (shown in FIG. 1 and described herein).

At an operation 52, the pressure regulator toggles to the second (open) mode. In some embodiments, operation 52 is performed by a pressure regulator the same as or similar to pressure regulator 20, (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A device configured to enhance cough flow of a subject, the device comprising;
   a subject interface configured to communicate with an airway of the subject;
   a pressure regulator configured to selectively control flow through the subject interface, the pressure regulator operating in (i) a first mode in which the subject interface is closed such that substantially no gas is communicated with the airway of the subject therethrough, and (ii) a second mode in which the subject interface is opened to permit gas to be exhausted from the airway of the subject through the subject interface; and
   a controller configured to successively toggle the pressure regulator between the first mode and the second mode during an individual exhalation of the subject, to cause a series of exsufflation events to occur during the individual exhalation of the subject, wherein the controller comprises one or more processors configured to execute computer program modules, the computer program modules comprising:
      a pressurization module configured to receive, from a user control interface, information indicating that the subject has pressurized the subject interface, the information including an input by the subject to the user control interface; and
      a control module configured to control operation of the pressure regulator between the first mode and the second mode to exsufflate the subject, wherein the control module is configured to exsufflate the subject by placing the pressure regulator in the first mode until a determination by the pressurization module that the subject has pressurized the subject interface, and, responsive to such a determination, to cause a series of exsufflation events over an individual exhalation of the subject through the subject interface by toggling, based on a user setting, the pressure regulator between the first mode and the second mode during the individual exhalation.

2. The device of claim 1, further comprising one or more sensors configured to generate output signals conveying information related to one or more gas parameters within the subject interface, and wherein the pressurization module is configured such that the information indicating whether the user has pressurized the subject interface comprises the output signals.

3. The device of claim 2, further comprising a cough initiation module configured to detect a cough trigger event, wherein the cough trigger event is determined based on the output signals of the sensors.

4. The device of claim 1, wherein the control module is configured to toggle the pressure regulator between the first mode and the second mode at a regular frequency to create the exsufflation events.

5. The device of claim 1, further comprising one or more sensors configured to generate output signals conveying information related to one or more gas parameters within the subject interface, and wherein the control module is configured such that during the series of exsufflation events the timing of one or both of transitions between the first mode and the second mode and/or transitions between the second mode and the first mode are determined based on the output signals.

6. The device of claim 1, wherein the user setting corresponds to setting, for each exsufflation event, a transition from the first mode to the second mode to occur at a predetermined time.

7. The device of claim 1, wherein a first exsufflation event at a beginning of the individual exhalation has a longer duration than a second exsufflation event at an end of the individual exhalation.

8. The device of claim 1, wherein the user control interface is a gesture recognition device configured to detect a facial movement of the subject, the facial movement corresponding to the input indicating that the subject has pressurized the subject interface.

9. A method for controlling a cough flow enhancement device, the method comprising:
   interfacing with a subject interface, an airway of the subject;
   operating a pressure regulator in a first mode in which the subject interface is closed such that substantially no gas is communicated with the airway of the subject therethrough;
   receiving, from a user control interface, information indicating pressurization of the subject interface by the subject, the information including an input by the subject to the user control interface; and
   responsive to a determination that the subject has pressurized the subject interface, successively toggling, based on a user setting, the pressure regulator between the first mode and a second mode during a single exhalation of the subject, to create a series of exsufflation events to occur during the single exhalation, wherein in the second mode the subject interface is opened to permit gas to be exhausted from the airway of the subject through the subject interface.

10. The method of claim 9, further comprising generating output signals conveying information related to one or more gas parameters within the subject interface, and wherein information indicating whether the user has pressurized the subject interface comprises the output signals.

11. The method of claim 9, wherein the series of exsufflation events are created by toggling the pressure regulator between the first mode and the second mode at a regular frequency.

12. The method of claim 9, further comprising generating output signals conveying information related to one or more gas parameters within the subject interface, and wherein during the series of exsufflation events the timing of one or both of transitions between the first mode and the second mode and/or transitions between the second mode and the first mode are determined based on the output signals.

13. A system configured to enhance a cough flow of a subject, the system comprising:
   means for communicating with an airway of the subject;
   means for selectively controlling flow through the means for communicating, the means for selectively regulating flow operating in (i) a first mode in which the means for communicating is closed such that substantially no gas is communicated with the airway of the subject therethrough, and (ii) a second mode in which the means for communicating is opened to permit gas to be exhausted from the airway of the subject through the means for communicating;
   means for receiving information indicating that the subject has pressurized the means for communicating, the information including an input by the subject to a means for accepting user input to the system; and
   means for controlling operation of the means for selectively controlling flow between the first mode and the second mode to exsufflate the subject, wherein the means for controlling the means for selectively regulating exsufflates the subject by placing the means for selectively regulating in the first mode until a determination that the subject has pressurized the means for communicating, and, responsive to such a determination, successively toggling, based on a user setting, the means for regulating between the first mode and the second mode during an individual exhalation of the subject, to create a series of exsufflation events to occur during the individual exhalation.

14. The system of claim 13, further comprising means for generating output signals conveying information related to one or more gas parameters within the means for communicating, and wherein the information indicating whether the user has pressurized the means for communicating comprises the output signals.

15. The system of claim 13, wherein the means for controlling toggles the means for selectively regulating between the first mode and the second mode at a regular frequency to create the exsufflation events.

* * * * *